United States Patent [19]

Stanke et al.

[11] Patent Number: 6,019,000
[45] Date of Patent: Feb. 1, 2000

[54] IN-SITU MEASUREMENT OF DEPOSITION ON REACTOR CHAMBER MEMBERS

[75] Inventors: Fred E Stanke, Cupertino; Butrus T. Khuri-Yakub, Palo Alto; Fahrettin Levent Degertekin, Millbrae; Hung Pham, San Jose, all of Calif.

[73] Assignees: Sensys Instruments Corporation, Santa Clara; The Board of Trustees of the Leland Stanford Junior University, Palo Alto, both of Calif.

[21] Appl. No.: 08/975,531

[22] Filed: Nov. 20, 1997

[51] Int. Cl.⁷ .................................................. G01N 9/24
[52] U.S. Cl. .............................. 73/622; 73/622; 73/624; 73/625
[58] Field of Search .............................. 73/597, 598, 602, 73/620, 627, 628, 643, 655, 657, 571, 629, 622, 624, 625, 617, 644; 376/252, 245; 976/DIG. 232

[56] References Cited

U.S. PATENT DOCUMENTS

| | | | |
|---|---|---|---|
| 4,106,327 | 8/1978 | Adler et al. | 73/1 DV |
| 4,437,332 | 3/1984 | Pittaro | 73/1 DV |
| 4,513,384 | 4/1985 | Rosencwaig | 364/563 |
| 4,658,649 | 4/1987 | Brook | 73/624 |
| 4,789,969 | 12/1988 | Naville | 367/36 |
| 4,803,884 | 2/1989 | Kaneta et al. | 73/598 |
| 4,843,884 | 7/1989 | House et al. | 73/622 |
| 4,899,589 | 2/1990 | Thompson et al. | 73/597 |
| 4,928,269 | 5/1990 | Kimball et al. | 367/35 |
| 5,159,838 | 11/1992 | Lynnworth | 73/644 |
| 5,216,638 | 6/1993 | Wright | 367/35 |
| 5,240,552 | 8/1993 | Yu et al. | 156/636 |
| 5,249,466 | 10/1993 | Jones | 73/633 |
| 5,271,274 | 12/1993 | Khuri-Yakub et al. | 73/597 |
| 5,305,641 | 4/1994 | Kuramochi et al. | 73/598 |
| 5,438,872 | 8/1995 | Kobayashi et al. | 73/597 |
| 5,439,551 | 8/1995 | Meikle et al. | 156/626.1 |
| 5,469,742 | 11/1995 | Lee et al. | 73/597 |
| 5,546,811 | 8/1996 | Rogers et al. | 73/800 |
| 5,557,970 | 9/1996 | Abbate et al. | 73/597 |
| 5,585,921 | 12/1996 | Pepper et al. | 356/357 |
| 5,604,592 | 2/1997 | Kotidis et al. | 356/357 |
| 5,607,236 | 3/1997 | Takagi et al. | 374/117 |

*Primary Examiner*—Hezron Williams
*Assistant Examiner*—Thuy Vinh Tran
*Attorney, Agent, or Firm*—Flehr Hohbach Test Albritton & Herbert LLP

[57] ABSTRACT

A system is disclosed that employs ultrasonic waves to perform in-situ measurements to determine the properties of films deposited on substrates in the course of various semiconductor or processing steps. In one embodiment a single transducer excites incident acoustic waves at multiple frequencies that reflect from the films. The reflected waves are received by the same transducer. An analysis system determines the phase shift of the received reflected waves and, based on the phase shift, determines the film properties. Other embodiments employ distinct source and receiving transducers. Embodiments are also disclosed that compensate the measured phase shift for temperature variations in the substrate. In one such system, temperature compensation is performed based on the processing of phase measurements made at multiple frequencies or incidence angles or with multiple ultrasonic modes. The disclosed techniques are equally applicable to determining the degree of erosion of chamber members.

20 Claims, 7 Drawing Sheets

IN-SITU MEASUREMENT OF DEPOSITION ON REACTOR CHAMBER MEMBERS

The present invention relates generally to ultrasonic transducers and particularly to transducers that use ultrasonic energy to determine the thickness of a material deposited on a reactor chamber member.

BACKGROUND OF THE INVENTION

Depositions on chamber members (e.g., walls, shields, windows, etc.) are an important issue in the semiconductor manufacturing process as these depositions can be a source of particle generation or alter the process plasma and thus can affect process conditions. Periodic cleaning of chamber member depositions in a chamber is therefore a necessary part of the semiconductor manufacturing process. In some cases there can be excessive cleaning of the chamber, where not only the deposition but some of the chamber itself is eroded. Presently, there are no systems that perform in situ measurement of the deposition on the chamber or direct measurement of the removal of the film or chamber erosion.

Therefore, it is an object of the present invention to provide a sensor that can perform in-situ measurement of the thickness of chamber member deposition to determine if a cleaning process is required, when a cleaning process has been completed and when chamber erosion has occurred. It is also an object of the present invention to provide temperature compensation techniques that allow the sensor to yield reliable film thickness measurements for the wide range of temperatures that can occur in a reactor chamber.

SUMMARY OF THE INVENTION

In summary, the present invention is an apparatus and method for measuring the properties of films deposited on reactor chamber members and the erosion of chamber members used in semiconductor manufacturing. In particular, the present invention includes an ultrasonic measurement apparatus that transmits ultrasonic waves into a chamber member on which a film is deposited and determines the film thickness deposited or degree of member erosion from the ultrasonic waves reflected from the film.

A preferred embodiment of the present invention includes one or more ultrasonic transducers coupled to one side of the member on whose other side there is deposition or erosion. The ultrasonic transducers can be either piezoelectric or electro-mechanical/acoustic transducers (EMAT) and can be attached to the member permanently (e.g., with epoxy) or temporarily (e.g., using a Hertzian contact). In a preferred embodiment the transducer elements are not directly coupled to the member, but are mounted on a buffer rod, which contacts the member.

The ultrasonic waves used to perform the measurement can be shear, or compressional waves that are transmitted into the member at normal or oblique incidence. If normal incidence is used, a single transducer can be used to both excite the waves and detect the return of the reflected waves. If oblique incidence is used, one transducer is used to excite the waves in the member and another transducer is used to detect the reflected waves at a different position in the member. In a preferred embodiment, measurements are made using ultrasonic waves at multiple frequencies to provide reliability in the presence of cyclic shifts and other artifacts that can occur as the film thickness changes during the deposition process.

The chamber members on which deposits and erosion can be measured with the present invention include chamber walls, shields, windows, shower heads, collimators, gas distribution plates and any other surface upon which unwanted deposits build up during processing. Additionally, the techniques of the present invention are applicable to the in-situ characterization of a film on any type of substrate. Other uses of the present invention include measuring erosion of the chamber members due to over-etching during chamber wall cleaning and measuring properties other than thickness of the substrates and any films deposited thereon. These other properties can include temperature, degree of polymerization and structural defects.

In a preferred embodiment the effects of temperature of the component are removed from the thickness measurement. One way of doing this involves performing a self-compensating measurement using ultrasonic waves at more than one frequency, or more than one angle of incidence, or more than one mode of propagation. The preferred embodiment employs mixed mode transducers that are capable of simultaneously exciting two modes (i.e., both shear and compressional modes), which reduces the number of required transducers. Other alternatives for temperature compensation include: comparing measurements made at two locations on the member with substantially similar temperatures, one where there is film buildup and one where there is none; and measuring the temperature independently, e.g., by using an acoustic thermometer or a thermocouple.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENTS

Before the preferred embodiments are described, the following glossary is provided to define some of the terms associated with the present invention.

Glossary

Calibration a characterization step that is performed on a test object when all relevant operating conditions are known. The idea of the calibration measurement is to account for test object-to-test object differences by determining for each individual test object being processed the measurements that result from characterizing that test object for the known operating conditions and to determine therefrom individual acoustic wave propagation characteristics in that test object. These characteristics are used to estimate an unknown process condition from characterization measurements made during a processing step in a processing chamber.

Characterization Sensitivity the inverse operator of the effect of operating conditions on a measurement.

Deposition generalized term meaning deposition of films on a member or erosion of the member, which is deposition with a negative thickness.

Echo an acoustic wave reflected away from a boundary (e.g., the end of a buffer rod) in response to an incident acoustic wave interacting with the test object.

Composite Reflection an echo resulting from reflection from multiple boundaries, e.g., all the boundaries in a stack of films. It includes the effects of multiple reflections between the multiple boundaries.

Lamb Wave an acoustic wave in thin substrates. Lamb wave modes are dispersive.

Receiver a generic term for a system that can sense acoustic waves in a target. The receiver might be a buffer rod, a laser-based sensing device or any other appropriate technology.

Setup a means of removing the characteristics of the transducers (sources and receivers) from the measurements intended to characterize the test object. Typically a setup measurement is made for known test object characteristics and subtracted from measurements made for test objects with unknown characteristics.

Source a generic term for a system that can excite acoustic waves in a target. The source might be a buffer rod, a laser-based excitation device or any other appropriate technology.

Transmission Profile an intermediate result derived from a waveform prior to calculating a measurement that is inverted by a characterization sensitivity.

The present invention builds on concepts described in U.S. Pat. No. 5,271,274 ("the '274 patent") and in the co-pending, cross-referenced application 08/847,144, both of which are entirely incorporated herein by reference. Basic concepts of the '274 patent and the cross-referenced application are now briefly summarized.

U.S. Pat. No. 5,271,274

U.S. Pat. No. 5,271,274 ("Thin Film Process Monitoring Techniques using Acoustic Waves) describes a system and method for measuring the thickness of at least one film on a substrate by propagating an acoustic wave through the film on the substrate. The incident acoustic wave generates reflected waves from both surfaces of the film that are received by an acoustic transducer. The thickness of the film is then determined in one of three ways: (1) from the time lapse between the propagation of the wave and the receipt of the reflected wave, (2) from the frequency domain of the reflected wave, or (3) from the phase of the reflected wave. The teachings of this patent are generally applicable to determining the thickness of a film on any type of substrate. However, the '274 patent does not describe improvements disclosed herein specifically related to use upon chamber members. Chamber members are generally thicker than silicon wafers, and are generally composed of polycrystalline materials rather than a single crystal. For the current application, stability of the measurement over hours, days, weeks, or even months is critical for its success, whereas measurements on wafers need be stable only for typical wafer processing times, i.e., minutes.

Polycrystalline materials generally attenuate ultrasound more rapidly than single crystals. This attenuation generally increases rapidly as a function of frequency. Thus in many cases attenuation at high frequencies in chamber members limits the highest frequency which can be used in the measurement. Ways (1) and (2) above generally assume that the wavelength of the ultrasound at the highest frequency is much less than the film thickness, and thus are frequently not suitable for film thicknesses of the order of 1 micron on chamber walls. Way (3) has the specific limitation that phase is not a monotonic function of thickness because of 360 degree ambiguities (phase wraps). The current invention discloses a means of making unambiguous thickness measurements from a plurality of frequencies.

The '274 patent does not disclose means for correcting way (3) for variations in the temperature of the substrate. This is potentially a greater problem for the current application, because the greater thickness of chamber members relative to silicon wafers allows for a greater effect of temperature on signals passing through the substrate. Furthermore, way (3) is significantly more susceptible to errors caused by changes in substrate temperature than either of ways (1) or (2). The present invention discloses techniques for compensating the acoustic measurements for the effects of temperature variations with either an independent measurement of temperature or with multiple independent acoustic measurements.

The '274 patent uses Hertzian contact buffer rods for making short-time measurements on many wafers with the same transducer. In general, it is difficult to distinguish changes in the acoustic properties of the Hertzian contact from deposition or erosion. Any changes in the Hertzian contact over time due to thermal expansion or mechanical relaxation in the apparatus which supports both the wafer and buffer rod lead to instabilities in the measurement. In the current application, permanently affixing the transducer, either with or without a buffer rod, to the substrate (chamber member) is both possible and desirable to achieve long term stability.

Similar concepts are also disclosed in U.S. Pat. No. 5,240,552 ("Chemical Mechanical Planarization (CMP) of a Semiconductor Wafer using Acoustical Waves for In-Situ End Point Detection").

Cross-Referenced Application 08/847,144

The cross-referenced application describes a variety of ultrasonic characterization systems variously employing digital measurements, frequency domain signal processing, perturbation analysis, and calibration and setup schemes that can be used to correct for measurement artifacts attributable to the transducers used to make the measurements and different processing chambers/environments in which the measurements are made.

The cross-referenced application is primarily directed to the use of Lamb waves excited and detected by pin transducers to interrogate a test object. Because it embodies different measurement geometries and techniques, the present invention does not generally employ Lamb waves, but shear and/or compressional waves. Nor, for the same reasons, is the present invention directed to the use of pin transducers, which generally have a high aspect ratio (i.e., are much longer than thick) and a cross-section in contact with the test object that is much smaller than one wavelength. However, these differences aside, the digital signal processing techniques described in the cross-referenced application are applicable to the present invention.

A goal of the invention described in application 08/847,144 is to estimate the operating condition, expressed as the vector O of the test object from a vector of measurements M based on processing the waveform group. The strategy is to estimate perturbations of the operating condition from some setup condition $M_0$ (in which a group of setup waveforms were recorded) via perturbations in the measurements. Processing of each waveform group yields a vector of $N_M$ measurements $M=\{M_i\}$, $i=1,2,\ldots,N_M$. The measurements might be functions of the phases of various Fourier spectral components of waveforms in the group, or functions of one or more times of arrival, e.g., the times of selected zero crossings. The processing of a setup waveform gives the setup measurement $M_O$. The operating condition $O=\{O_j\}$, $j=1,2,\ldots,N_O$ includes implicitly only those conditions that are of interest. Candidates for specific operating conditions as members of the vector include:

(1) the test object's temperature, (2) the pins' separation, (3) the test object's thickness, and (4) the properties of layers on the test object (e.g., thickness or state of polymerization).

It is possible for O to have a single member, e.g., the test object's temperature or thickness. All candidate conditions that are not included in O are assumed to be known and invariant, or irrelevant. The setup operating condition $O_0$ must be known, a priori, and other operating conditions are to be estimated. The measurement perturbation $\mu=M-M_0$ is related to the operating perturbation $o=O=O_0$ by a function $\Lambda$, such that $\mu=\Lambda(o)$, which is determined by the physics of the acoustic waves used for the measurement. The acoustic characterization of the test object is performed by inverting the function $\Lambda$ to obtain a characterization sensitivity $\Lambda^{-1}$ which, along with the measurement perturbation and setup operating condition yields the operating condition matrix $O=\Lambda^{-1}(\mu)+O_0$. Any intermediate results of processing waveforms to yield measurements are termed transmission profiles.

The teachings of the cross-referenced application can be used in the present invention to derive film properties (e.g., thickness) using digital signal processing techniques based on signals from one or more transducers. The preferred embodiments of the present invention are now described.

The Preferred Embodiments

Figure 1A:
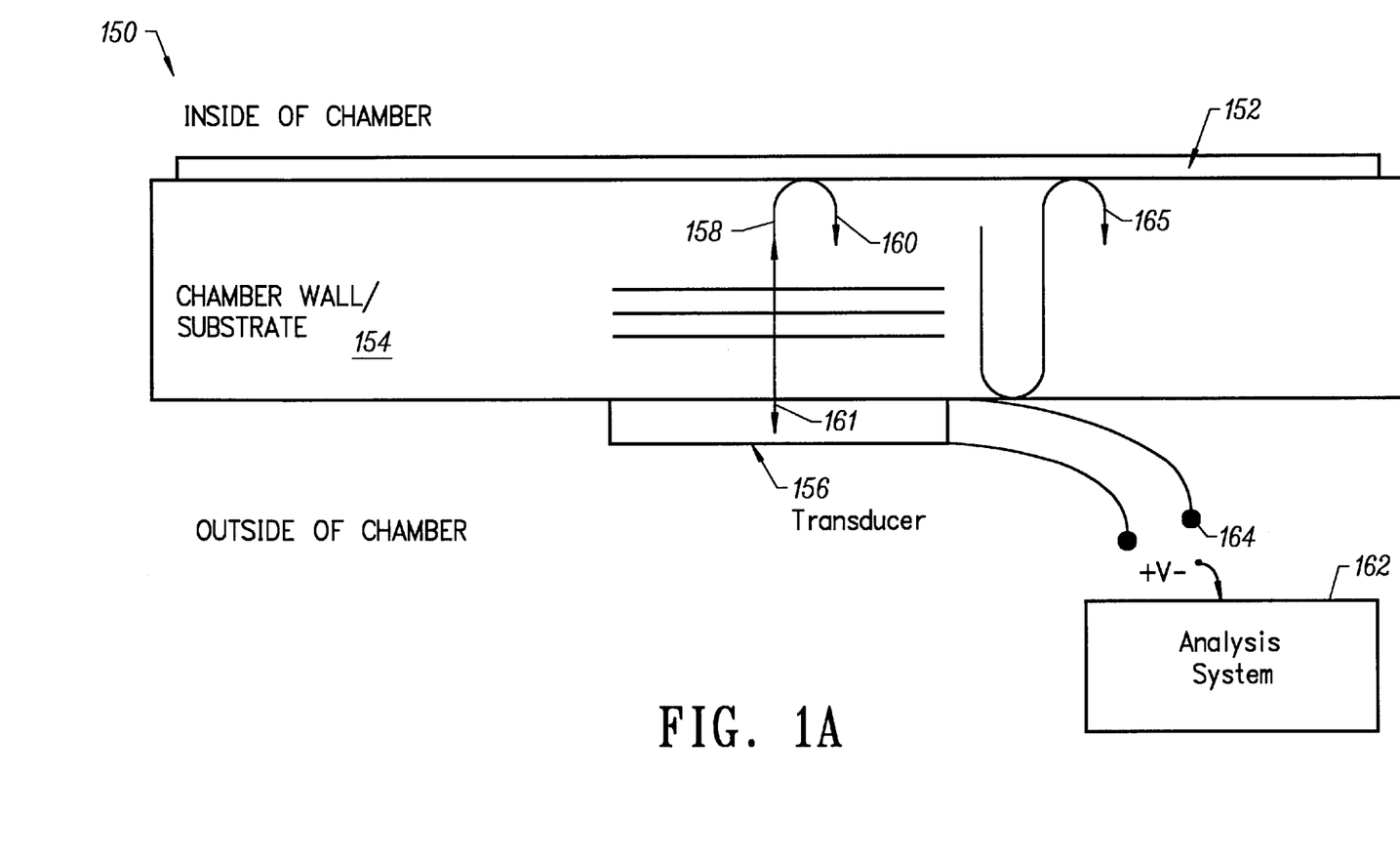
FIG. 1A is a diagram of a generic embodiment of the present invention wherein the thickness of polymer depositions on a chamber member is measured using an ultrasonic transducer.

Referring to FIG. 1A, there is shown a diagram of a generic embodiment 150 of the present invention wherein the thickness of depositions 152 on a chamber member 154 is measured using a single ultrasonic transducer 156. In this system, an incident ultrasonic wave 158 excited by the transducer 156 travels through the chamber member 154 and is reflected from both surfaces of the polymer film 152, giving rise to a compound reflected wave 160. Multiples 165 of the waves 160 result from additional reflections within the substrate from the films and the interface between the transducer 156 and the chamber member 164. The incident wave 158 also generates echo waves 161 that are reflected from the interface between the transducer 156 and the chamber member 154. The reflected wave 160 and echo waves 161 are received by the transducer 156. An analysis system 162 is configured to receive signals 164 from the transducer 156 corresponding to the receipt at the transducer of manifestations of the reflected wave 160 and, optionally, the echo waves 161, the initial excitation of the transducer 156 and the multiples 165.

Typically, the transducer 156 is a piezoelectric transducer and the ultrasonic waves 158, 160, 161, 165 are shear or compressional waves. Alternatively, the transducer could be an EMAT; and the waves could be any type of wave that can be supported in the test object 154. The chamber member 154 on which the film 152 is deposited can be a chamber wall, shield, window, shower head, collimator, gas distribution plate or any other surface upon which unwanted deposits build up during processing. More generally, the present invention is applicable to any type of substrate (e.g., wafers) that might be used in semiconductor or other processing. The film 152 can be any material that is deposited on the chamber member or substrate 154 during an etch or deposition process or any cleaning process. Due to the thickness of some chamber members, which discourages the propagation of high frequencies (i.e., frequencies in the hundreds of MHz or GHz range), the frequency range of operation of the transducer 156 is typically between approximately 1 and 120 MHz. However, higher frequencies can be used if allowed by the dimensions and acoustic properties of the chamber member of interest, e.g., the '274 patent.

Figure 1B:
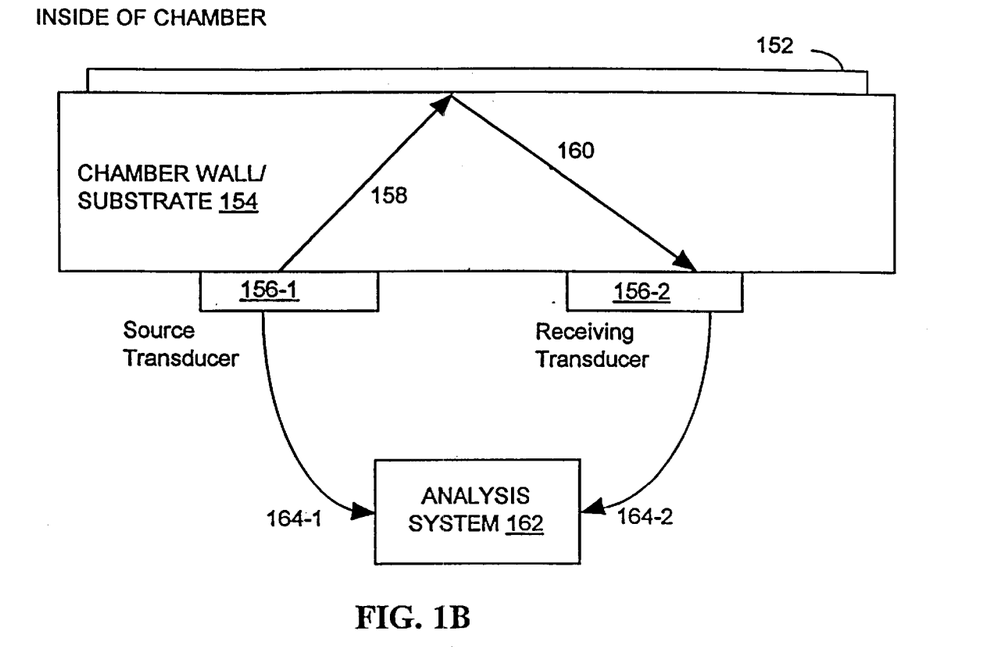
FIG. 1B is a diagram of a generic embodiment of the present invention wherein the thickness of polymer depositions on a chamber member is measured using more than one ultrasonic transducer.

Referring to FIG. 1B, another generic embodiment of the present invention is shown where different source and receiving transducers 156-1, 156-2 are used instead of a single transducer. The same basic measurement techniques are applicable to the embodiments of FIGS. 1A and 1B, with the obvious difference that the angle of incidence in the embodiment of FIG. 1A is normal whereas it is oblique in the embodiment of FIG. 1B. Another difference between the two generic embodiment is that Lamb waves can be employed in the embodiment of FIG. 1B in addition to shear and compressional waves. As is well known, Lamb waves are plate modes (i.e., exist in the entire cross-section of a plate) and therefore have propagation characteristics that depend on plate characteristics such as temperature, the thickness of the plate and any films deposited thereon. Lamb waves are less useful in the embodiment of FIG. 1A as they would not produce a distinct reflected wave 160 as required by the embodiment of FIG. 1A. Apart from these differences, and others that may be noted, all aspects of the present disclosure are applicable to both embodiments.

Using methods described in the '274 patent and the 08/847,144 application, the analysis system 162 uses at least a subset of the signals 164, the waveform group, to determine the phase shift of the reflected wave 160 in the presence of the film 152 as compared to the phase of the reflected wave 160 when there is no film present (determined, e.g., at the beginning of deposition). The phase shift of the reflected wave 160 is a function of the frequency and the thickness of the film 152. The transducer 156 is preferably excited with a broad band pulse to allow for analysis at multiple frequencies. The relationship between frequency, film thickness and phase shift is now described in reference to FIG. 2.

Figure 2:
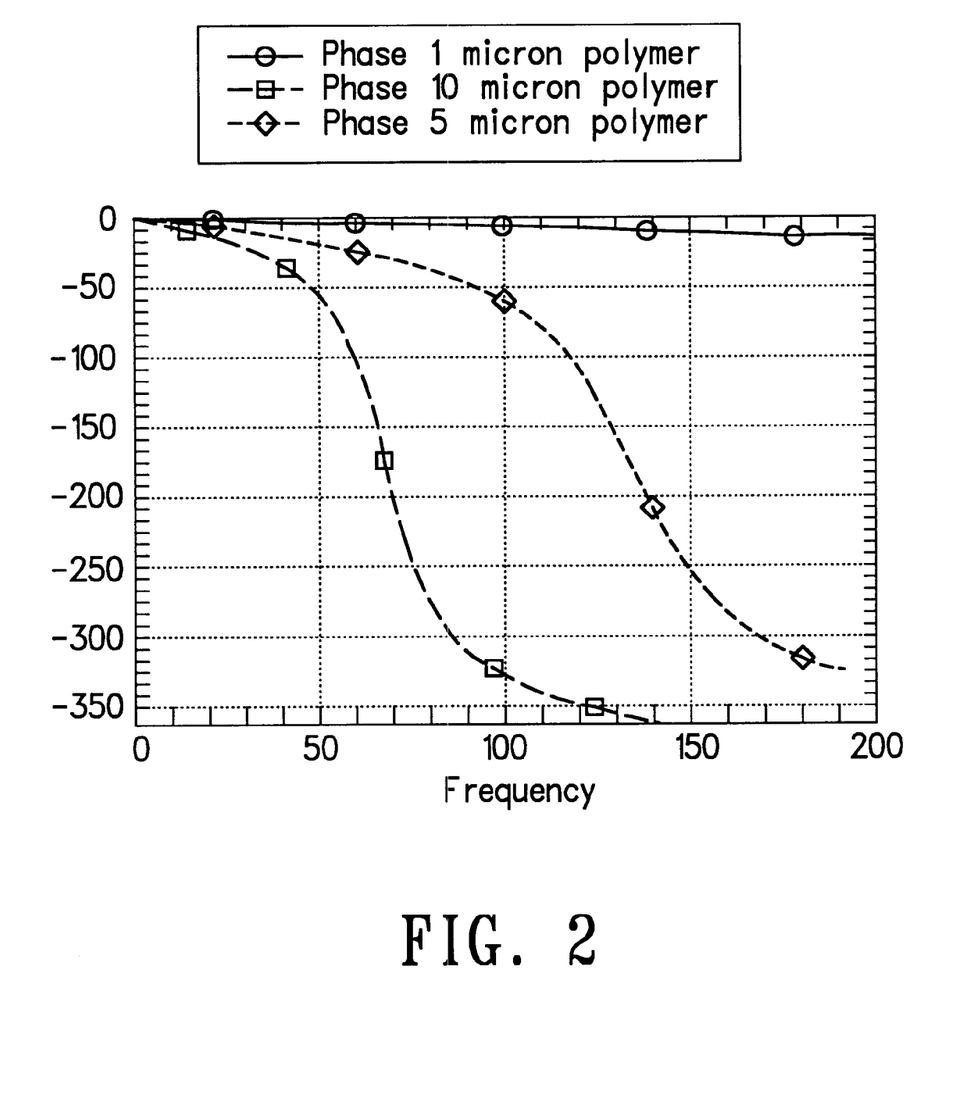
FIG. 2 is a plot of phase shift (degrees) versus frequency of a composite reflection from polymer films of different thicknesses (1 micron, 5 micron, 10 micron)
Figure 3:
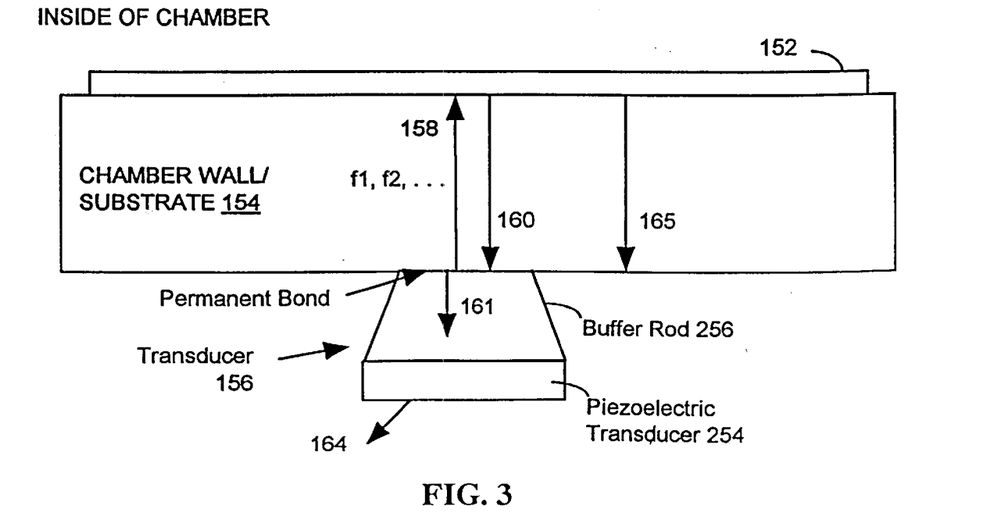
FIG. 3 is a diagram of a preferred embodiment of the present invention, in which the ultrasonic transducer comprises a transducer element affixed to a buffer rod that contacts a chamber member.

Referring to FIG. 2, there is shown a plot of phase shift versus frequency of ultrasonic waves in polymer films of different thicknesses (1 micron, 5 micron, 10 micron). The curves shown in FIG. 3 are the results of theoretical calculations. Note that, for the thinnest (1 micron) film, the phase shift is about 6 degrees at 100 MHz. Thus, assuming that the analysis system 162 is capable of measuring a phase shift of 0.1 degree, it should be possible to measure a change in film thickness of 167 Angstroms. As shown in FIG. 2, increasing the frequency of operation enhances the measurement resolution.

For the thicker films (5 and 10 micron) a cyclic change occurs in the phase shift when the phase reaches 360 degrees or some multiple thereof. Thus, if measurements are being made at a single wavelength, it is necessary that the analysis system 162 makes the measurements continually in order to detect the cyclic phase shifts as the film thickness changes, which may not be possible for the time scales associated with the current invention. Alternatively, the analysis system 162 can make measurements at multiple frequencies, some of which would not experience a cyclic change at any given film thickness. Due to these cyclic changes and other characteristics of the chamber member 154 that can render phase measurements made at a single frequency unreliable, the preferred embodiment simultaneously makes each phase measurement at multiple frequencies.

The analysis system 162 can employ other methods to measure the film thickness that do not depend on a direct measurement of phase shift, but which interpret the received signals 164 in light of variations in the reflected wave 160 (which are due to the presence of the film 152 on the surface of the chamber member 154). In another alternative, the frequency of the resonance of the composite structure (transducer, member and film) can be measured and related to film properties, e.g., thickness. In this case, the ordinate in FIG. 2 is accurately interpreted as frequency-thickness product, and the phase is held constant by compensating for thickness changes with inversely proportional changes in frequency. Additionally, analog signal processing is possible using tools such as tone bursts and quadrature detectors.

In another alternative method, the analysis system 162 can digitize the signals 164 and use digital signal processing techniques to extract the film information. Possible digital signal processing techniques include spectral estimation using Fourier transforms, or system modeling (e.g., with the well known auto-regressive, moving-average model). Many applicable digital signal processing techniques are described in the cross-referenced application.

Referring again to FIG. 1, the present invention is also applicable to chamber members 154 that are compound structures having multiple layers of solids or solids and liquids. In this case, care must be exercised to insure that the portion of the received signal that is processed is indeed from the surface of the chamber member 154 on which there is a deposited film 152.

The frequency of the incident waves 158 is chosen based on the phase precision of the measurement system, phase sensitivity to film thickness and chamber member temperature, the pulse length necessary to insure that the reflection 160 from the surface with film buildup is separable from other pulses, the minimum and maximum film thicknesses of interest, and the frequency dependent attenuation in the member and/or film.

In the simplest applications of the present invention, the acoustic properties (i.e., propagation characteristics) of the film 152 are known, in which case only a single measurement is needed to measure the film thickness (in addition to measurements needed to remove spurious effects, e.g., those due to temperature). In some cases, especially during calibration of the analysis system 162, it may be necessary to measure the acoustic properties of the film 152. One approach is to combine the results of multiple acoustic experiments (e.g., experiments made at multiple angles of incidence), to measure the film's properties and thickness simultaneously. Calibration and setup measurement techniques are described in detail in the cross-referenced application. In the preferred implementation, calibration relates to measuring the temperature sensitivity of the particular transducer(s) 156 and member 154.

Referring to FIG. 3, there is shown a diagram of a preferred embodiment in which the ultrasonic transducer 156 comprises a transducer element 254 affixed to a buffer rod 256 that contacts the chamber member 258. Generally, a buffer rod 256 has a roughly 1:1 aspect ratio and has a cross-section in contact with the chamber member that is much larger than a wavelength. Film thickness measurements are performed with the preferred embodiment in the same manner as described for the generic embodiment of FIG. 1. For the reasons set out above, in the preferred embodiment phase shifts are made at multiple frequencies fi. In the preferred embodiment, the waves 158, 160, 161 comprise two modes (shear and compressional). Due to the need for measurement stability over periods of as long as a month, which approximates a typical interval between chamber cleanings, the buffer rod 256 is permanently mounted to the chamber member 258. The analysis system 162 can compute the phase shift from a subset (the waveform group) of the signals 164 representing any combination of the waves 158, 160, 161, 165; however it is preferred to use only the compound reflected and echo waves 160, 161. In the present application, Lambda ($\Lambda$) is preferably not linearized and is determined from a mixture of theoretical and physical experiments relevant to a particular instance of the apparatus. Setup can be performed when the apparatus is initially installed, and thereafter at convenient times, e.g., after a chamber has been opened and thoroughly wet cleaned.

Figure 4:
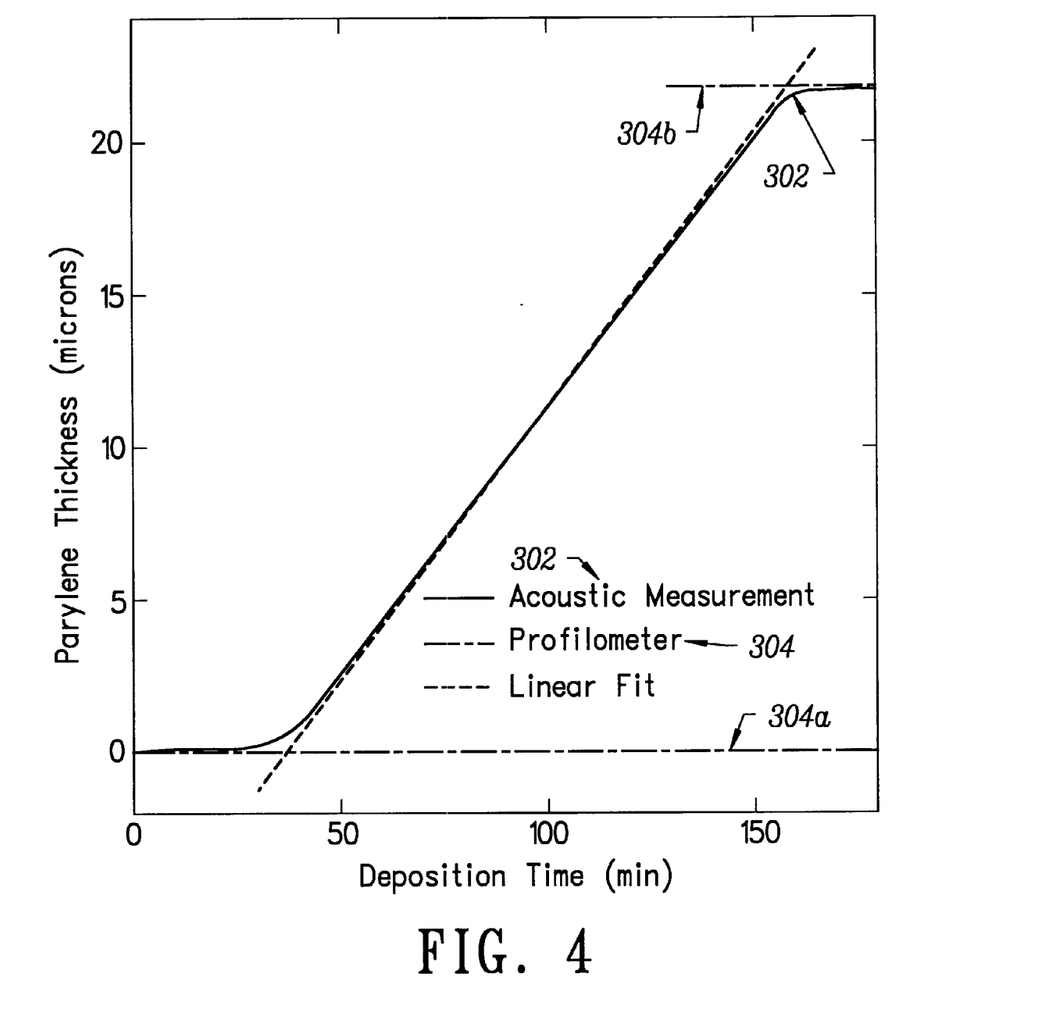
FIG. 4 shows plots of parylene deposition thickness on aluminum nitride measured using techniques of the present invention.

Referring FIG. 4, there are shown plots 302, 304 of parylene deposition thickness on aluminum nitride as measured in accordance with the present invention. These are actual experimental results gathered during a parylene deposition process. Aluminum nitride, which is a ceramic, was selected as representative of the materials used for chamber walls. These results are generalizable to other ceramics, fused quartz, aluminum, stainless steel, and other materials used in the fabrication of chamber members and other substrates. The baseline parylene thickness, indicated by line 304a, was 0 microns before deposition. During deposition, the thickness of the parylene on the aluminum nitride was continually measured in-situ; results of this measurement are shown on the plot 302. There is no other measurement of the thickness during deposition. Line 304c is a best fit to the acoustic measurement over the range where there is apparently uniform deposition, i.e., from thicknesses of 5 microns to 20 microns. The line suggests that the deposition was indeed uniform, and that the measurement accurately indicates this. After the deposition, the final thickness of the parylene was measured by removing the deposited parylene over some region and profiling the step between that region and a neighboring region having the full deposited thickness. This profile thickness is indicated by line 304b, and is in agreement with the final thickness measured acoustically. This agreement demonstrates the accuracy of the measurement.

Because the phase velocity of the ultrasonic waves 158, 160, 161, 165 can depend on the temperature of the test object 154 in which the waves are propagating, it is preferable to remove the effects of the temperature of the chamber member from the film thickness measurement. Temperature compensation can be performed in several different ways described in reference to FIGS. 5A–5C.

Figure 5A:
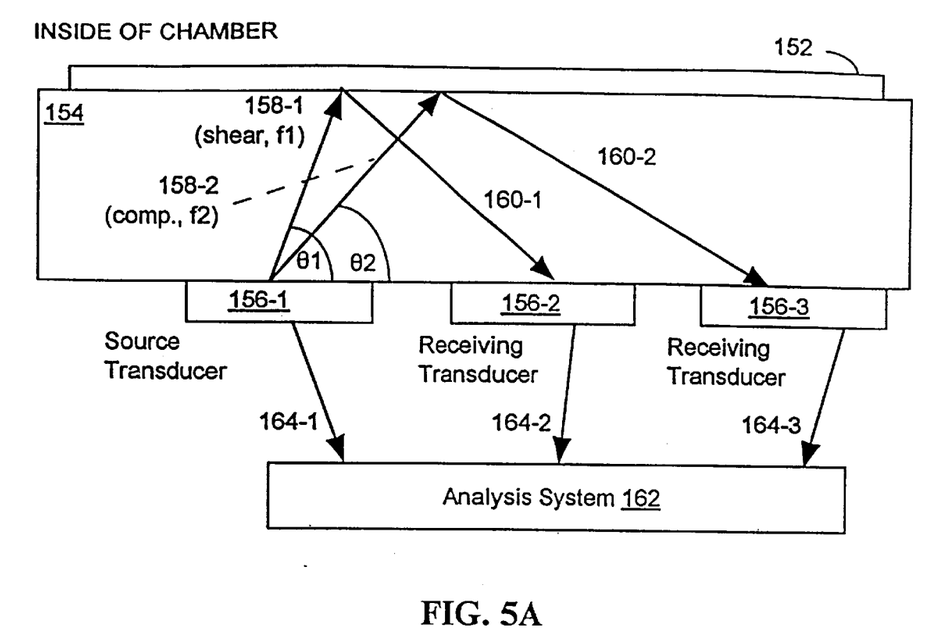
FIG. 5A is a diagram of a first ultrasonic sensor apparatus configured to make temperature-compensated measurements.

Referring to FIG. 5A, there is illustrated a first temperature compensation approach in which the measurement itself is made self-compensating by using one or more transducers 156 operating at any combination of:

(1) more than one frequency f1, f2, . . . ;

(2) more than one angle of incidence θ1, θ2, . . . ; and (3) more than one mode of propagation (e.g., "shear" and "compressional", referring to different waves).

As described in the cross-referenced application, making multiple simultaneous measurements enables multiple test object characteristics (such as temperature and film thickness) to be determined simultaneously as long as the effects of the characteristics on the measurements are sufficiently independent. Thus, making multiple measurements also allows the known effects of temperature to be separated from the effects on the measurement of film thickness, which is the variable of interest.

The particular embodiment of FIG. 5A includes one mixed mode source transducer 156-1 that excites shear and compressional modes 158-1, 158-2 at different respective incidence angles θ1, θ2 and two receiving transducers, 156-2, 156-3, which receive reflected waves 160-1, 160-2 generated by the respective modes. The transducers can operate at one or more frequencies f1, f2, etc. Other variations of the system of FIG. 5A are possible, including sensor systems with:

(1) a single transducer 156 acting as source and receiver that operates at multiple frequencies f1, f2, . . . and normal incidence and is single mode, meaning that it excites a single ultrasonic mode; and (2) a single transducer 156 acting as source and receiver that operates at multiple frequencies f1, f2, . . . and normal incidence and is mixed mode, meaning that it excites two different ultrasonic modes (e.g, shear and compressional modes).

These configurations are merely exemplary and are not intended to limit the scope of the present invention.

Figure 5B:
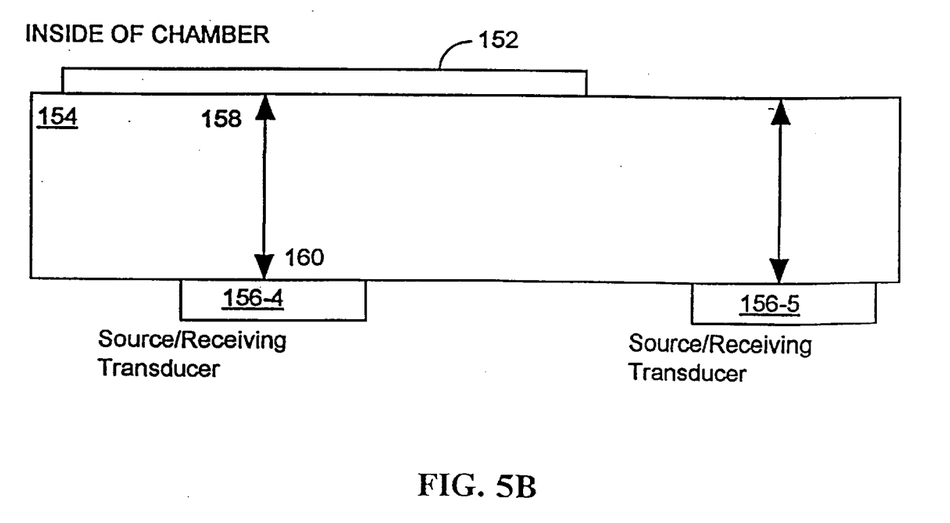
FIG. 5B is a diagram of a second ultrasonic sensor apparatus configured to make temperature-compensated measurements.

Referring to FIG. 5B, a second temperature compensation approach involves mounting two transducers 156-4, 156-5 on the chamber member 154, one positioned where there is film 152 buildup and one where there is no film buildup. In the second approach thickness measurements are made using both transducers 156-4, 156-5 and the measurements are compared to determine the film thickness (e.g., the difference in the measurements being due to the film thickness).

Figure 5C:
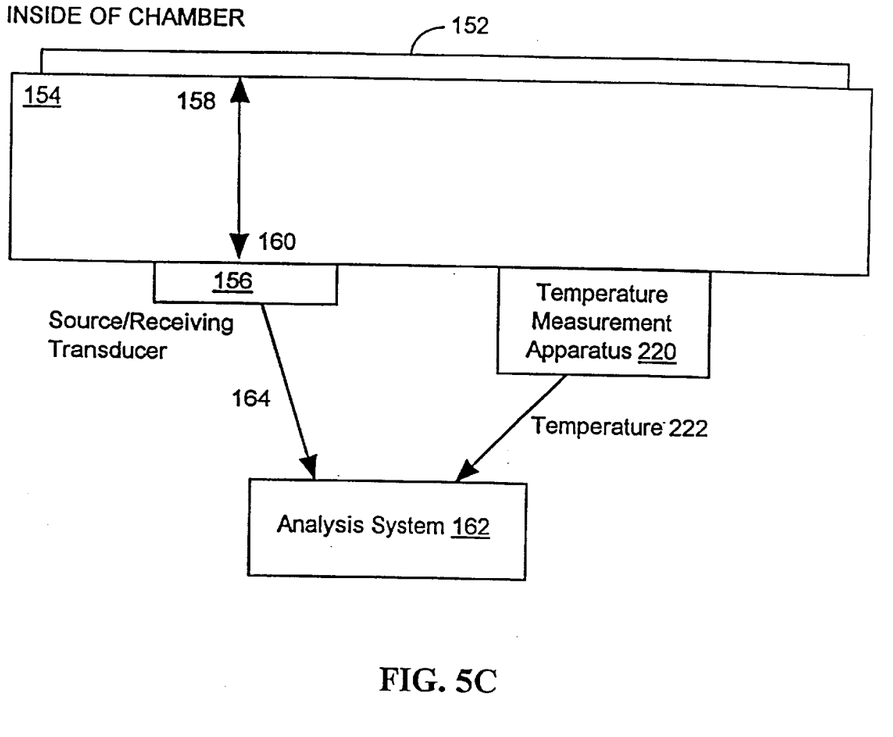
FIG. 5C is a diagram of a third ultrasonic sensor apparatus configured to make temperature-compensated measurements.

Referring to FIG. 5C, a third temperature compensation approach involves measuring the temperature of the of the chamber member 154 independently, e.g., by using a thermocouple, resistance-temperature device, or acoustic thermometer 220. The analysis system 162, based on the signals 164 and temperature 222, computes a temperature-corrected phase shift based on the known effects of temperature on the propagation of the waves 158, 160, 165. The advantages of temperature compensation are now described in reference to FIG. 6.

Figure 6:
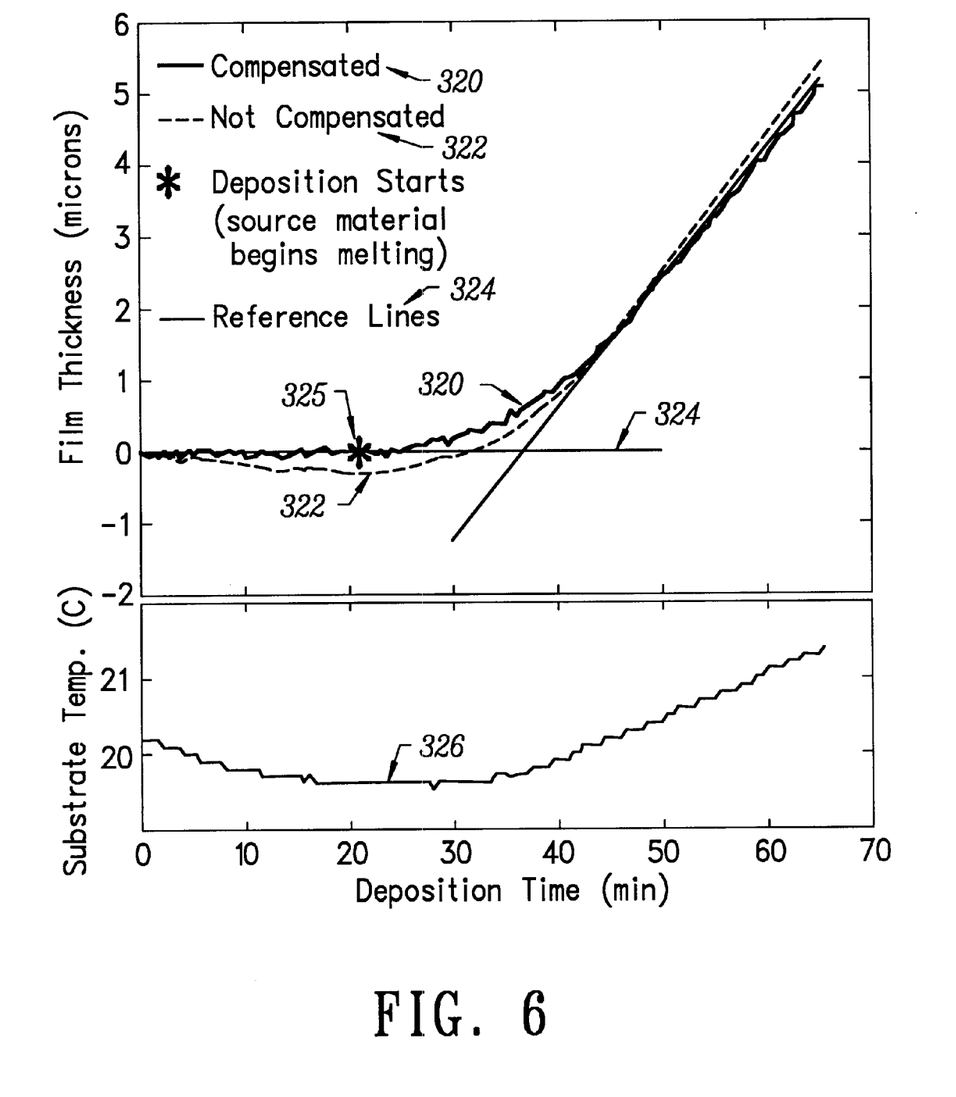
FIG. 6 shows plots of deposition thickness (microns) versus deposition time (minutes) for temperature compensated and un-compensated measurements made using the techniques of the present invention.

Referring to FIG. 6, there are shown plots 320, 322 of deposition thickness (microns) versus deposition time (minutes) for compensated and uncompensated measurements made in accordance with the present invention and a zero reference 324 for comparison. The measurements for both plots 320, 322 were made during a deposition step during which the substrate temperature varied as shown in the temperature trace 326 at the bottom of FIG. 6. The plots 320, 322 correspond respectively to compensated and uncompensated measurements. Note that the uncompensated measurement indicates erosion or negative deposition, which is not physically possible in this case, and is therefore a measurement error. This error visibly correlates in time with the indicated changes in temperature, and is interpreted as being caused by the changes in temperature. The compensated measurement accurately tracks zero thickness 324 until the onset of deposition at time 325, indicating the efficacy of the temperature compensation techniques of the present invention.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

For example, the preferred embodiments described herein are directed to buffer rods; however, the teachings of the present invention can be implemented using any combination of sources and receivers that are able, respectively, to excite and detect acoustic waves in a target object (such as a chamber member). A good candidate for the source (corresponding to a piezo-electric transducer and buffer) is a laser that generates a beam directed to an excitation point on the target object where the acoustic waves are to be excited. In this alternative embodiment, heating of the target at the excitation point excites the desired acoustic waves. Good candidates for the receiver (corresponding to the piezo-electric transducer and buffer) include laser detectors consisting of either a knife edge or an interferometer that measures deflection of the target object at a detection point caused by arrival of acoustic waves thereat. Another example of a modification would be to use amplitude or attenuation coefficient as a measurement. This would be consistent with interpreting velocity generally as complex velocity, as is known in the art.

In another alternative embodiment, the film thickness on a member of interest can be monitored indirectly, by using the present invention to monitor the film thickness on another member configured for in-situ film thickness measurement.

What is claimed is:

1. An apparatus for measuring properties including thickness of one or more films on a chamber member, comprising:

one or more source transducers, each configured to excite acoustic waves at a plurality of frequencies in the substrate at a corresponding excitation location;

one or more receiving transducers, each configured to detect acoustic waves at a probe location in the substrate, wherein the acoustic waves include reflected waves received at the probe location due to a composite reflection of the excited acoustic waves from the one or more films, wherein the one or more source and the one or more receiving transducers are not necessarily different transducers and the probe and excitation locations are not necessarily different locations; and a processing module coupled to the receiving transducers configured to determine the properties of the one or more films from measurements including a phase measurement at each of a plurality of frequencies on a selected waveform group.

2. The apparatus of claim 1, wherein the chamber member comprises a one of:

a chamber wall;

a shield;

a window;

a shower head;

a collimator; and a gas distribution plate.

3. The apparatus of claim 1, wherein the plurality of frequencies are between 1 MHz and 120 MHz.

4. The apparatus of claim 1, wherein the one or more source and the one or more receiving transducers comprise a single transducer.

5. The apparatus of claim 1, wherein the processing module and the transducers are used to determine degree of erosion of the chamber member due to over-etching caused by a cleaning process used to clean the chamber member.

6. An apparatus for measuring properties of one or more films on a substrate while compensating for temperature differences in the substrate, comprising:

one or more source transducers, each configured to excite acoustic waves in the substrate at a corresponding excitation location;

one or more receiving transducers, each configured to detect acoustic waves at a probe location in the substrate, wherein the acoustic waves include reflected waves received at the probe location due to reflection of the excited acoustic waves from the one or more films, wherein the one or more source and the one or more receiving transducers are not necessarily different transducers and the probe and excitation locations are not necessarily different locations; and a processing module coupled to the receiving transducers configured to determine the properties of the one or more films from measurements on a selected waveform group;

wherein at least one of the one or more source transducers, the one or more receiving transducers, and processing module are configured to compensate for the effects of the temperature differences in the substrate when determining the film properties;

wherein the one or more receiving transducers and the one or more source transducers are configured to compensate for the effects of the temperature differences by respectively exciting and receiving waves characterized by a plurality of acoustic modes; and wherein the processing module is configured to compensate for the effects of the temperature differences by inverting the measurements with the plurality of modes for the film properties and temperature.

7. The apparatus of claim 6, wherein the measurements include a phase measurement.

8. The apparatus of claim 6, wherein the properties include thickness.

9. The apparatus of claim 6, wherein:

the one or more receiving transducers and the one or more source transducers are configured to compensate for the effects of the temperature differences by respectively exciting and receiving the waves at a plurality of incident angles; and the processing module is configured to compensate for the effects of the temperature differences by inverting the measurements at the plurality of angles for the film properties and temperature.

10. The apparatus of claim 6, wherein the plurality of modes comprise shear and compressional modes.

11. The apparatus of claim 6, wherein:

the one or more receiving transducers, the one or more source transducers and the processing module are configured so that a first phase measurement is made in an area where there is no film buildup and a second phase measurement is made in an area where there is film buildup; and the processing module is further configured to derive the properties by comparing the first and second phase measurements.

12. The apparatus of claim 6, wherein the processing module and the transducers are used to determine degree of erosion of the substrate due to over-etching caused by a cleaning process used to clean the chamber member.

13. An apparatus for measuring properties of one or more films on a chamber member, comprising:

one or more transducers, each configured to excite acoustic waves in the member and to detect acoustic waves at a probe location in the substrate, wherein the acoustic waves include reflected waves received due to reflection of the excited acoustic waves from the one or more films; and a processing module coupled to the transducers configured to determine from measurements on a selected waveform group degree of erosion of the chamber member due to over-etching caused by a cleaning process used to clean the chamber member.

14. The apparatus of claim 13, wherein the measurements include a phase measurement.

15. The apparatus of claim 13, wherein the processing module and the transducers are used to determine an endpoint of a chamber cleaning process.

16. The apparatus of claim 13, wherein the processing module and the transducers are used to determine the properties of the one or more films.

17. The apparatus of claim 13, wherein the transducers are bonded to the chamber member.

18. The apparatus of claim 16, wherein the film properties comprise film thickness.

19. The apparatus of claim 16, wherein the processing module and the transducers are configured to provide stable measurements of the film properties over a period of weeks.

20. The apparatus of claim 16, wherein the measurements of the film properties are used to determine when chamber cleaning is required.

* * * * *